(12) United States Patent
Nativ et al.

(10) Patent No.: US 10,888,320 B2
(45) Date of Patent: Jan. 12, 2021

(54) HYPOTHERMIC CIRCULAR SURGICAL STAPLERS AND METHODS OF USE

(71) Applicant: Ethicon, Inc., Somerville, NJ (US)

(72) Inventors: Nir I. Nativ, West Orange, NJ (US); Leo B. Kriksunov, Ithaca, NY (US); Robert J. Tannhauser, Bridgewater, NJ (US); Silvia Chen, Kendall Park, NJ (US)

(73) Assignee: Ethicon, Inc., Somerville, NJ (US)

( * ) Notice: Subject to any disclaimer, the term of this patent is extended or adjusted under 35 U.S.C. 154(b) by 246 days.

(21) Appl. No.: 15/789,055

(22) Filed: Oct. 20, 2017

(65) Prior Publication Data

US 2019/0117220 A1  Apr. 25, 2019

(51) Int. Cl.
*A61B 17/068* (2006.01)
*A61F 7/12* (2006.01)
(Continued)

(52) U.S. Cl.
CPC ........ *A61B 17/0684* (2013.01); *A61B 17/072* (2013.01); *A61B 17/07207* (2013.01); *A61B 17/115* (2013.01); *A61B 17/1155* (2013.01); *A61F 7/12* (2013.01); *A61B 17/10* (2013.01); *A61B 18/1445* (2013.01); *A61B 34/70* (2016.02); *A61B 2017/00092* (2013.01); *A61B 2017/07257* (2013.01); *A61B 2017/07271* (2013.01); *A61B 2018/00011* (2013.01); *A61B 2018/00023* (2013.01); *A61B 2018/00047* (2013.01); *A61B 2018/00791* (2013.01);
(Continued)

(58) Field of Classification Search
CPC .............. A61B 17/0684; A61B 17/072; A61B 17/1155; A61B 17/10; A61B 18/1445; A61B 2017/00092; A61B 2017/07257; A61B 2017/07271; A61B 2018/00011; A61B 2018/00023; A61B 2018/00047; A61B 2018/00791; A61B 34/70; A61F 7/12; A61F 2007/0056; A61F 2007/0057; A61F 2007/0075; A61F 2007/0096; A61F 2007/126
USPC ...................................... 227/176.1
See application file for complete search history.

(56) References Cited

U.S. PATENT DOCUMENTS 3,794,039 A  2/1974 Kollner et al.
4,281,785 A  8/1981 Brooks
(Continued)

OTHER PUBLICATIONS

International Search Report dated Jan. 30, 2019 for International Application No. PCT/US2018/055868.

*Primary Examiner* — Chelsea E Stinson
*Assistant Examiner* — Himchan Song
(74) *Attorney, Agent, or Firm* — David R. Crichton; Leo B. Kriksunov

(57) ABSTRACT

The present invention relates to surgical instruments and methods for enhancing properties of tissue repaired or joined by surgical staples and, more particularly to surgical instruments and methods designed to enhance the properties of repaired or adjoined tissue at a target surgical site, especially when sealing an anastomosis between adjacent intestinal sections to improve tissue viability under hypoxia conditions, prevent tissue inflammation, and to prevent leakage. The present invention further relates to hypothermic circular stapling instruments configured to pre-cool the tissues being joined by staples.

11 Claims, 14 Drawing Sheets

(51) Int. Cl.
  *A61B 17/072* (2006.01)
  *A61B 17/115* (2006.01)
  *A61B 18/00* (2006.01)
  *A61B 17/00* (2006.01)
  *A61F 7/00* (2006.01)
  *A61B 34/00* (2016.01)
  *A61B 17/10* (2006.01)
  *A61B 18/14* (2006.01)

(52) U.S. Cl.
  CPC ............... *A61F 2007/0056* (2013.01); *A61F 2007/0057* (2013.01); *A61F 2007/0075* (2013.01); *A61F 2007/0096* (2013.01); *A61F 2007/126* (2013.01)

(56) References Cited

U.S. PATENT DOCUMENTS

| | | | |
|---|---|---|---|
| 5,173,133 A | 12/1992 | Morin et al. | |
| 5,211,646 A | 5/1993 | Alperovich et al. | |
| 5,271,544 A | 12/1993 | Fox et al. | |
| 5,807,393 A | 9/1998 | Williamson, IV et al. | |
| 5,906,625 A | 5/1999 | Bito et al. | |
| 6,656,177 B2 | 12/2003 | Truckai et al. | |
| 6,694,984 B2 | 2/2004 | Habib | |
| 7,169,146 B2 | 1/2007 | Truckai et al. | |
| 7,762,445 B2 | 7/2010 | Heinrich et al. | |
| 7,815,641 B2 | 10/2010 | Dodde et al. | |
| 8,647,336 B2* | 2/2014 | Werneth | A61B 18/02 606/23 |
| 8,679,114 B2 | 3/2014 | Chapman et al. | |
| 8,715,277 B2 | 5/2014 | Weizman | |
| 8,911,486 B1 | 12/2014 | Drnek et al. | |
| 9,005,199 B2 | 4/2015 | Beckman et al. | |
| 9,044,261 B2* | 6/2015 | Houser | A61B 17/29 |
| 9,259,265 B2 | 2/2016 | Harris et al. | |
| 9,295,514 B2 | 3/2016 | Shelton, IV et al. | |
| 2002/0022829 A1* | 2/2002 | Nagase | A61B 18/20 606/12 |
| 2002/0032440 A1* | 3/2002 | Hooven | A61B 18/1445 606/41 |
| 2003/0024538 A1* | 2/2003 | Edwards | A61B 18/1492 128/898 |
| 2007/0135803 A1* | 6/2007 | Belson | A61B 5/064 606/1 |
| 2007/0262116 A1* | 11/2007 | Hueil | B25C 5/0292 227/175.1 |
| 2009/0048589 A1* | 2/2009 | Takashino | A61B 18/1445 606/28 |
| 2011/0306967 A1* | 12/2011 | Payne | A61B 18/1445 606/41 |
| 2012/0053577 A1* | 3/2012 | Lee | A61B 18/1815 606/33 |
| 2012/0089047 A1* | 4/2012 | Ryba | A61B 18/02 600/554 |
| 2014/0046411 A1* | 2/2014 | Elkins | A61F 7/0085 607/104 |
| 2014/0094790 A1* | 4/2014 | Hafner | A61B 18/1482 606/33 |
| 2014/0180281 A1* | 6/2014 | Rusin | A61B 34/76 606/45 |
| 2014/0371735 A1 | 12/2014 | Long | |
| 2016/0120601 A1 | 5/2016 | Boudreaux et al. | |
| 2017/0112560 A1* | 4/2017 | Ross | A61B 18/1445 |
| 2017/0165105 A1* | 6/2017 | Anderson | A61N 5/0616 |
| 2019/0200977 A1* | 7/2019 | Shelton, IV | A61B 17/07207 |

* cited by examiner

HYPOTHERMIC CIRCULAR SURGICAL STAPLERS AND METHODS OF USE

FIELD OF THE INVENTION

The present invention relates to surgical instruments and methods for enhancing properties of tissue repaired or joined by surgical staples and, more particularly to surgical instruments and methods designed to pre-cool the tissues being joined by staples to improve outcomes for the repaired or adjoined tissue at a target surgical site.

BACKGROUND OF THE INVENTION

The medical field has utilized various techniques to join or bond body tissue together. Historically, suturing was the accepted technique for rejoining severed tissues and closing wounds. Suturing is achieved with a surgical needle and a suturing thread, with the intended function of sutures to hold the edges of a wound or tissue against one another during the healing process. Staples have been used in certain situations to replace suturing thread when joining or anastomosing various body structures, such as, for example, the bowel. The surgical stapling devices employed to apply staples are generally designed to simultaneously cut and seal an extended segment of tissue in a patient.

Linear or annular/circular surgical stapling devices are employed by surgeons to sequentially or simultaneously apply one or more rows of surgical fasteners, e.g., staples, to body tissue to join segments of body tissue together and/or for the creation of an anastomosis. Linear surgical stapling devices generally include a pair of jaws or finger-like structures between which body tissue to be joined is placed. When the surgical stapling device is actuated, firing bars move longitudinally and contact staple drive members in one of the jaws, and surgical staples are pushed through the body tissue and into and against an anvil in the opposite jaw thereby crimping the staples closed. A knife blade may be provided to cut between the rows/lines of staples.

Annular or circular surgical stapling devices generally include an annular staple cartridge assembly including a plurality of annular rows of staples (typically two or three), an anvil assembly operatively associated with the annular cartridge assembly, and an annular blade disposed internal of the rows of staples. In general, an end-to-end anastomosis stapler typically places an array or group of staples into the approximated sections of a patient's bowels or other tubular organs. The resulting anastomosis contains an inverted section of bowel which contains numerous "B" shaped staples to maintain a secure connection between the approximated sections of bowel.

Post-operative leakage of the stapled tissue seals, has been shown to lead to morbidity and mortality. Although the etiology of the leak is unclear and likely to be multifactorial, sealants, e.g., synthetic or biological sealants, have been applied to the surgical site to guard against leakage. The sealants are typically applied to the outer surface of the anastomosis in a separate step. Many technologies are related to direct application of material to the serosal layer after stapling by either dripping or spraying. The problems associated with these techniques are that access is very difficult and visual assessment as to whether the material was applied to the right spot and completely around the anastomosis. The material is also applied on surface of the serosal layer when the target site is subserosal along the staple line. Applying a therapeutic agent to the serosal layer of the colon requires the therapeutic agent to penetrate through the serosa and to the staple region, then provide a biological affect, and overcome the problems associated with a leak formation, all within 24-48 hours, assuming the material was applied to the correct spot intraoperatively. One of the most challenging steps in the application of a topical adjunctive therapy to the serosa side of a colorectal anastomosis is the application the material to the actual staple line that is deep within the pelvic canal (for example, lower anterior resection.).

U.S. Pat. No. 5,173,133 "METHOD FOR ANNEALING STAPLER ANVILS" discloses a method for annealing a delimited portion of an anvil member for use in a surgical stapler, said method comprising: a) providing a means for heating; b) placing said anvil member in cradle means, said cradle means comprising a member fabricated from a thermally conductive material and possessing means configured and dimensioned to receive said anvil such that a first part of the exterior surface of the anvil is in thermally conductive contact with the interior surface of the receiving means and a second part of the exterior surface of the anvil is exposed; c) positioning said cradle in proximity to said heating means such that the delimited portion of the second part of the exterior surface of the anvil member is within the heating range of said heating means; and d) operating said heating means such that the delimited exposed portion of the anvil member is heated to an annealing temperature.

U.S. Pat. No. 9,005,199 "Heat management configurations for controlling heat dissipation from electrosurgical instruments" discloses a surgical instrument, comprising: an end effector comprising: a first jaw comprising an electrode having a distal end; a second jaw, wherein the first jaw and the second jaw are operably coupled together; and a cutting member configured to translate between a retracted position and a fully advanced position with respect to the first jaw, wherein the cutting member comprises a cutting surface and a body, wherein the body defines a cavity and at least one opening communicating with the cavity, and wherein the at least one cutting member opening is proximal to the distal end of the electrode when the cutting member is in the fully advanced position.

U.S. Pat. No. 8,679,114 "Incorporating rapid cooling in tissue fusion heating processes" discloses an electrode sealing assembly designed for use with an electrosurgical instrument for sealing tissue, comprising: first and second jaw members movable from a first position in spaced relation relative to one another to at least one second position for grasping tissue therebetween, the jaw members including: electrically conductive sealing plates disposed in opposing relation to one another, at least one jaw member including: a thermoelectric cooling plate having a first surface in direct contact with an outer surface of the sealing plate, the thermoelectric cooling plate including first and second electrical connections disposed on opposite sides of the thermoelectric cooling plate, the first connection configured to selectively transmit a first electrical potential and the second connection configured to selectively transmit a second electrical potential such that heat generated by the sealing plates is transferred away from the tissue via the thermoelectric cooling plate, wherein the electrically conductive seal plates each include inward lateral side edges, the inward lateral side edges and the first surface of the thermoelectric cooling plate configured to form a knife slot therebetween dimensioned to receive a knife blade therein, the knife blade disposed substantially adjacent and in proximity to the thermoelectric cooling plate to enable heat transfer from the knife blade to the thermoelectric cooling plate, and wherein the at least one jaw member further includes a first heat sink disposed in contact with a second surface of the thermoelectric cooling plate, the first heat sink made from a thermally conductive, electrically insulative cool polymer.

U.S. Pat. No. 7,815,641 "Surgical instrument and method for use thereof" discloses a surgical instrument for treating a tissue, comprising: a hand piece; and a tissue engaging portion arranged to be received by the hand piece, the tissue engaging portion comprising first and second opposed jaw members having an open position and a closed position for engaging the tissue therebetween, the first and second jaw members arranged to receive surgical energy from a surgical generator, and at least one cooling member spaced from at least one of the first and second jaw members, the at least one cooling member separately movable with respect to the jaw members and having an open position and a closed position for engaging the tissue, wherein positioning the jaw members in their closed position and applying surgical energy to the tissue allows for treatment of the tissue, and positioning the at least one cooling member in its closed position provides at least one of a pressure gradient or a thermal gradient between the jaw members and the at least one cooling member.

U.S. Patent Application Publication No. 2014/0180281 "ELECTRIC STAPLER DEVICE" discloses an end effector assembly of a forceps, comprising: first and second jaw members, at least one of the jaw members moveable relative to the other between a spaced-apart position and an approximated position for grasping tissue therebetween, each jaw member including: a plurality of spaced apart seal plates, wherein each seal plate corresponds to a seal plate on the opposite jaw member to form a pair of seal plates, each pair of seal plates is individually activatable; and a cutting element, wherein when the first and second jaw members are in the approximated position, the pairs of seal plates closer to the cutting element define a gap therebetween that is smaller than the gap between pairs of seal plates further from the cutting element.

U.S. Pat. No. 4,281,785 "Stapling apparatus and method and thermoplastic staples used therewith" discloses a stapling apparatus for stapling an assembly of components, said apparatus having a stapling head for carrying and serially dispensing a plurality of staples made entirely of thermoplastic material, each of said staples comprising a bight and a pair of legs extending in substantially parallel relation from opposite ends of said bight, staple driving means in said head for driving each of said staples through said assembly once each staple is dispensed into a driving position, and a clinching anvil for clinching outer portions of said legs of each staple, the improvement wherein said anvil has a heated portion comprising an integral heater for heat shaping said outer portions of said legs in clinched relation after disposal of said legs through said assembly and a cooled portion comprising an integral cooling device for cooling said outer portions of said legs after shaping thereof, and said apparatus comprising a single support for said anvil and its heated and cooled portions, said support being mounted for pivoting movements about a single pivot to enable movement of said heated portion into position to provide said heat shaping of said outer portions and then movement of said cooled portion into position to provide said cooling of said outer portions.

U.S. Pat. No. 7,169,146 "Electrosurgical probe and method of use" discloses an electrosurgical instrument for delivering energy to tissue, comprising: a working end for engaging the tissue; a surface layer at an exterior portion of the working end, the surface layer comprising a matrix of polymeric PTC composition adapted to deliver electrical current to the tissue; and a cooling structure at an interior portion of the working end; wherein the cooling structure cools the PTC matrix to lower the temperature of one or more portions of the PTC matrix.

U.S. Pat. No. 3,794,039 "APPARATUS FOR CRYOSURGERY" discloses an apparatus for cryosurgery having a central unit containing a supply of liquid cryogenic coolant, control and regulating means, and sub atmospheric suction means connected to a probe for freezing tissue, the improvement comprising: a. a cryogenic probe including a grip member having a hollow cryogenic coolant feed line supported by said grip member, said line being open at the tip thereof and connected at one end to said cryogenic coolant supply for transmitting liquid coolant to impinge directly upon tissue to be frozen; b. a hollow cryogenic coolant return line open at a transparent end thereof concentrically disposed around said feed line to form a space therebetween; and c. means communicating said space to said sub atmospheric suction means for returning vaporized coolant from said feed line, the open end of said feed line being recessed with respect to the corresponding open end of said return line.

U.S. Pat. No. 6,656,177 "Electrosurgical systems and techniques for sealing tissue" discloses a jaw assembly of a surgical instrument, comprising: an instrument working end carrying first and second jaws actuatable between a first open position and a second closed position, the jaws in the closed position defining a longitudinal axis and wherein the jaws further define exterior faces and interior jaw faces having a longitudinal length; an axially extending member that is actuatable from a first retracted position to a second extended position in an axial channel extending the length of the exterior and interior jaw faces; and wherein said axially extending member defines first cam surface portions that engage cooperating second cam surface portion that extend the entire length of the interior jaw faces to actuate the jaws toward the closed position and prevent flexing apart of said jaws.

U.S. Pat. No. 6,694,984 "Liver surgery" discloses a method of reducing blood loss during liver surgery, wherein diseased or damaged tissue is removed from the liver by delivery of thermal energy to the tissue by a probe, wherein the method is carried out to define liver resection with an at least 2 cm wide coagulative necrosis zone in surgery the improvement comprising: a multiprobe application followed by a scalpel division of the parenchyma and suture of blood vessels bigger than about 2.5 mm.

U.S. Patent Application Publication No. 2014/0371735 "ELECTROSURGICAL INSTRUMENT END EFFECTOR WITH PREHEATING ELEMENT" discloses an apparatus for operating on tissue, wherein the apparatus comprises an end effector, the end effector comprising: (a) a first jaw; (b) a second jaw, wherein the first jaw is selectively pivotable toward and away from the second jaw to capture tissue; (c) at least one preheating element, wherein the at least one preheating element is disposed within one or both of the first jaw or the second jaw, wherein the at least one preheating element is operable to heat up and thereby transfer heat to tissue captured between the first jaw and the second jaw through; and (d) at least one electrode, wherein the at least one electrode is operable to apply RF energy to tissue captured between the first jaw and the second jaw.

U.S. Patent Application Publication No. 2016/0120601 "ELECTROSURGICAL INSTRUMENT WITH SENSOR" discloses an apparatus for operating on tissue, the apparatus comprising: (a) a body; (b) a shaft extending distally from the body; (c) an end effector configured to receive energy from an energy source, wherein the end effector comprises: (i) a first jaw, and (ii) a second jaw, wherein the second jaw is pivotable relative to the first jaw to transition the end effector from an open configuration to a closed configuration, wherein the first jaw and second jaw define a closure gap between each other when the end effector is in the closed configuration; and (d) a sensor, wherein the sensor is operable to detect when the end effector is in the closed configuration, wherein the sensor is in communication with the energy source, wherein the sensor is operable to communicate a signal to the energy source when the sensor detects the end effector in the closed configuration.

U.S. Pat. No. 7,762,445 "Electrosurgical stapling apparatus" discloses a surgical stapler, comprising: an anvil member having a plurality of staple-forming recesses defined therein for deforming a corresponding plurality of surgical staples, the anvil includes an electrically insulative material disposed on a tissue contacting surface thereof, wherein at least one of the plurality of staple-forming recesses is coated with the electrically insulative material, wherein the electrically insulative material is selectively removable, and wherein the electrically insulative material is selectively removed from the tissue contacting surface of the anvil member during a firing of the surgical stapler; a cartridge assembly including a staple cartridge defining a tissue contact surface and configured to retain a plurality of electrically conductive surgical staples; an electrical conduit adapted for connection to a surgical generator; and an actuator operatively connected to the cartridge assembly for deploying the plurality of surgical staples from the staple cartridge against the anvil member, the actuator being movable within the cartridge assembly and coupled to the electrical conduit, the actuator including an electrically conductive actuation sled and an electrically conductive knife blade, wherein the electrical conduit is configured for transmitting a thermogenic energy to the knife blade and to the staples through the actuation sled.

U.S. Pat. No. 5,807,393 "Surgical tissue treating device with locking mechanism" discloses a surgical instrument comprising: a tissue treating portion including: a therapeutic energy delivering device arranged to deliver therapeutic energy to tissue, and a tissue manipulation device; a shaft coupled to said tissue treating portion, said shaft including a therapeutic energy communication device operatively coupled to said therapeutic energy delivering device said energy delivering device and said energy communication device adapted to be actuated to deliver therapeutic energy to tissue; a tissue manipulation actuating device having a locked position and an unlocked position, said tissue manipulation actuating device extending through said shaft and operatively coupled to said tissue manipulation device; a locking mechanism coupled to said tissue manipulation actuating device for moving said tissue manipulation actuating device from said locked position to said unlocked position after said therapeutic energy delivering device and said therapeutic energy communication device are actuated to deliver therapeutic energy to tissue; a tissue parameter measurement and instrument control device adapted to provide a feedback signal representative of a tissue treatment status of tissue being treated by said therapeutic energy delivering device, said parameter measurement and instrument control device coupled to said tissue treating portion of said instrument; and a status indicator coupled to said parameter measurement and instrument control device, said status indicator arranged to provide a user perceptible signal indicating a tissue treatment status.

U.S. Pat. No. 8,715,277 "Control of jaw compression in surgical instrument having end effector with opposing jaw members" discloses a surgical instrument comprising: an end effector comprising a distal end and a proximate end, wherein the end effector comprises: a first jaw member comprising a distal end and a proximate end, wherein the proximate end of the first jaw member comprises a pin; a second jaw member opposing the first jaw member, wherein the second jaw comprises a distal end and a proximate end, wherein the proximate end of the second jaw member comprises a multi-lobed cam slot with at least three lobes, wherein the pin of the first jaw member is disposed and moveable within the multi-lobed cam slot between the three lobes, wherein the first jaw member is moveable relative to the second jaw member such that the first and second jaw members are transitionable between an open position and a closed position, such that the first and second jaw members are in the open position when the pin of the first jaw member is in a first lobe of the multi-lobed cam slot and the first and second jaw members are in the closed position when the pin of the first jaw member is in a second lobe of the multi-lobed cam slot, and wherein the pin of the first jaw member moves into a third lobe of the multi-lobed cam slot when the pin transitions from the first lobe to the second lobe; and a latch at a distal end of the end effector for latching the distal end of the first jaw member to the distal end of the second jaw member when the first and second jaw members are in the closed position.

U.S. Pat. No. 9,259,265 "Surgical instruments for tensioning tissue" discloses an end-effector configured to be attached to a surgical instrument comprising a closure beam, the end-effector comprising: a first jaw comprising an electrode; a second jaw, wherein at least one of the first jaw and the second jaw is movable relative to the other jaw between an open position and a closed position, and wherein, in the closed position, a first region of tissue is configured to be positioned intermediate the first jaw and the second jaw and is configured to be compressed; the first jaw comprising: a first slider member movably attached to the first jaw and movable relative to the electrode and to the closure beam, wherein the first slider member comprises a first tissue-contacting surface configured to engage a second region of tissue; and the second jaw comprising: a second slider member movably attached to the second jaw and movable relative to the electrode and to the closure beam, wherein the second slider member comprises a second tissue-contacting surface configured to engage the second region of tissue; a longitudinal slot; and a cutting member slidable within the longitudinal slot; wherein the first slider member and the second slider member are configured to change the width of the end effector and apply a tensile stretching force to tissue positioned intermediate the first region of tissue and the second region of tissue when the first slider member and the second slider member are moved laterally relative to the electrode and to the longitudinal slot.

U.S. Pat. No. 8,911,486 "Implantable devices for thermal therapy and related methods" discloses a method of applying thermal therapy to tissue, comprising: forming a tissue opening in a patient to access a target site within the patient; passing a thermal device through the tissue opening; placing the thermal device at the target site; closing the tissue opening with the thermal device at the target site; after closing the tissue opening, applying or continuing to apply thermal therapy to the target site through the thermal device; and after closing the tissue opening, pulling a tether attached to the thermal device to remove the thermal device from the patient without reopening the tissue opening; wherein the thermal device comprises a malleable pad.

U.S. Pat. No. 9,295,514 "Surgical devices with close quarter articulation features" discloses an apparatus, comprising: a shaft section extending longitudinally along a first plane; an end effector comprising a first jaw and a second jaw configured to pivotally open and close in a second plane relative to the first plane about a pivot point, wherein the first plane is orthogonal to the second plane; an articulation section disposed between the shaft section and the end effector, the articulation section configured to articulate in the second plane relative to the first plane in response to a rotatable articulation control mechanism, the articulation section comprising a molded member that defines at least one slot and at least one recess; the at least one slot comprising a first slot extending longitudinally along the length of the molded member, the first slot comprising an opening at one side of the molded member and terminating within the molded member on another side; a longitudinally slidable blade comprising an upper flange and a lower flange; a flexible firing element comprising upper and lower flexible bands slidably positioned within the at least one slot, the upper flexible band connected to the upper flange of the blade and the lower flexible band connected to the lower flange of the blade; wherein at least one of the first and second jaws comprises an electrode.

U.S. Pat. No. 5,211,646 "Cryogenic scalpel" discloses a cryogenic scalpel for conducting surgical operations on parenchymatous biological tissues, comprising: a hollow housing having an interior space; a working portion connected to said hollow housing and having a body extending in a lengthwise direction; heat-exchanger means for establishing a zone for cooling biological tissues during surgery by supplying cooling fluid to said interior space; a blade having two ends and a cutting lip, said ends of said blade being secured to said heat-exchanger means; a coolant free to circulate through said heat-exchanger means; a piping accommodated in said interior space of said hollow housing and communicating with said heat-exchanger means; a source of electromechanical oscillations accommodated in said hollow housing to establish reciprocating motion to said working portion with a frequency of electromechanical oscillation with the result that heating of said blade is precluded and parenchymatous biological tissues are separated by simultaneously cooling in said cooling zone created by said heat-exchanger means; and means for imparting electromechanical oscillations to said working portion so as to transmit reciprocating motion to said blade; said means for imparting being connected between said source of electromagnetic oscillations and said blade.

SUMMARY OF THE INVENTION

The present invention relates to surgical instruments and methods for enhancing properties of tissue repaired or joined by surgical staples and, more particularly to surgical instruments and methods designed to enhance the properties of repaired or adjoined tissue at a target surgical site, especially when sealing an anastomosis between adjacent intestinal sections to improve tissue viability under hypoxia conditions, prevent tissue inflammation, and to prevent leakage.

The present invention, in one aspect, relates to a hypothermic circular surgical stapler for anastomotic joining of tissue having an anvil having an anvil tissue facing surface and an opposite distal end; the anvil having a peripheral staple bending zone on said anvil tissue facing surface; a cylindrical stapling head mounted on a support shaft, said stapling head containing a concentric knife and a plurality of deployable staples in concentric arrays within a stapling head tissue facing surface of said stapling head; a moveable shaft connecting the anvil and stapling head; and at least one cooled zone located inside the anvil in proximity to the anvil tissue facing surface and/or inside the stapling head in proximity to the stapling head tissue facing surface. The cooled zone can be a reservoir or compartment filled with a coolant, wherein said coolant could be a fluid having a high heat capacitance. The coolant can be at least partially frozen or a combination of a frozen coolant and a melted coolant. On a compositional basis, the coolant can be, in whole or part, water, alcohol, glycerol, ethylene glycol or mixtures thereof. In one compositional embodiment, the coolant can be a glycerol-water mixture having melting point above 0° C. but below 8° C. In another embodiment, the coolant can be an instant coolant.

The reservoir can in one alternative be connected to a recirculation pump and a chiller via a supply channel and a drain channel. In still further embodiments, the cooled zone can include a Peltier element or be a cooled zone with compressed gas-cooled throttling orifices connected to gas conduits and to a source of compressed gas. In a still further embodiment, the cooled zone can include a heat pipe configured to transfer thermal energy between the stapling head and/or the anvil and a cooling zone in a stapler handle. A thermally conductive zone can extend from being in contact with the reservoir towards the anvil tissue facing surface and/or towards the stapling head tissue facing surface. Optionally, the reservoir can have at least one window to enable visualization of the one or more coolants contained therein.

The present invention also relates to methods of establishing an anastomotic joint between tubular tissue lumens with the circular stapling instrument of claim 1, the method comprising the steps of: axially inserting the anvil into a tubular tissue T1 and closing the tissue T1 around the anvil; axially inserting the stapling head into a tubular tissue T2; connecting the anvil to the stapling head via the anvil shaft; approximating the anvil and the stapling head and compressing the tubular tissues T1 and T2 between the stapling head and the anvil; firing the anastomotic stapler and establishing a stapled anastomotic joint between the tissues T1 and T2; wherein the cooled zone is cooled prior to steps 1, and/or 2, and/or 3, and/or 4.

DETAILED DESCRIPTION OF THE INVENTION

Surgery often involves joining of two or more layers of tissue together with optional simultaneous sectioning of a portion of the tissue along the staple line. For example, colorectal surgery in many cases involves the resection of a segment of the colon and rectum. Following a colorectal resection, the colon and rectum are drawn together with a circular stapler and an end-to-end anastomosis is performed. Post-operative leakage of the anastomosis has been shown to lead to morbidity and mortality.

Conventional surgical stapling instruments have a staple-containing component and an opposing anvil component, between which at least two tissue layers to be joined are compressed prior to delivery of staples from the staple-containing component, whereby staples are piercing both tissue layers and are bent, deformed, or closed against the opposing anvil component.

Figure 1:
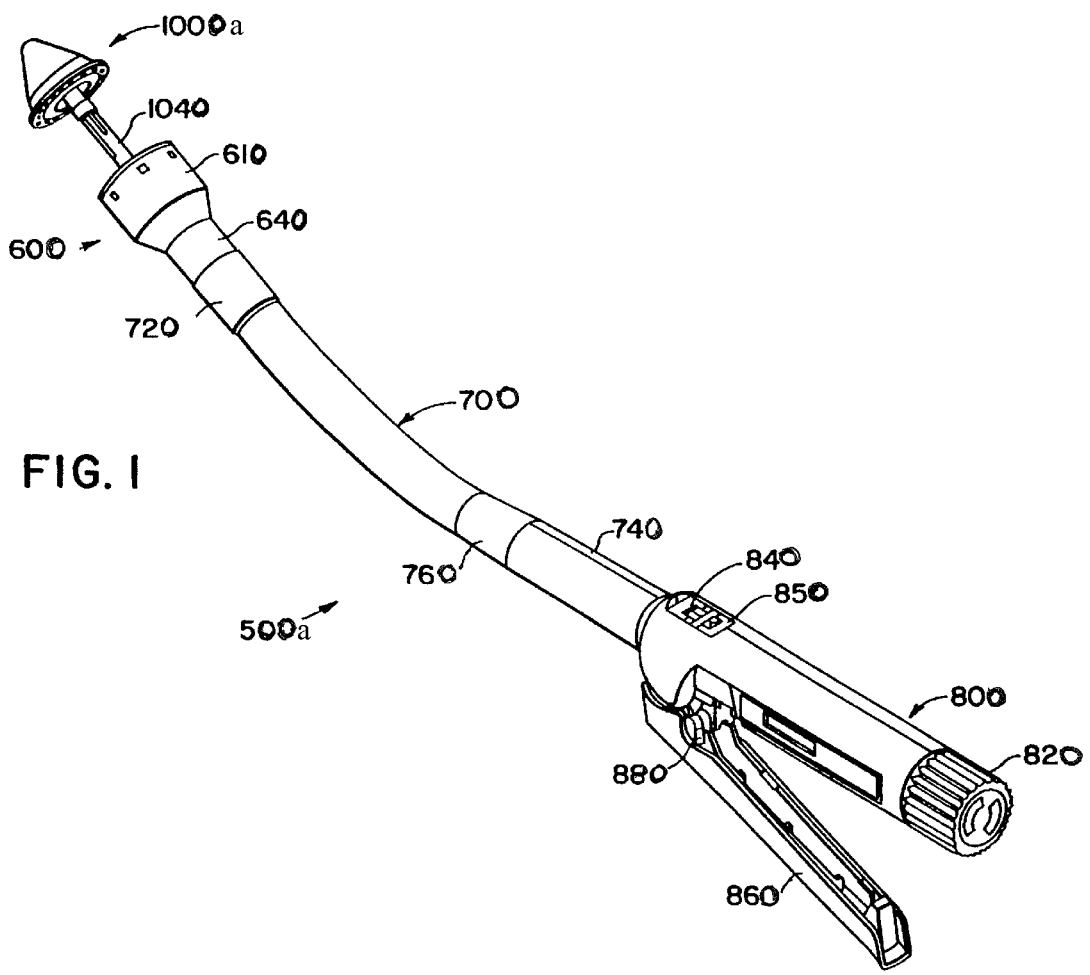
FIG. 1 shows a perspective view of a typical circular surgical stapling instrument.

Referring now to FIG. 1, a generic surgical anastomosis stapling instrument or stapling device for performing a circular anastomosis stapling operation is shown, with the figure taken from the U.S. Pat. No. 5,271,544 "Surgical anastomosis stapling instrument", assigned to Ethicon, Inc., Somerville, N.J., and incorporated herein by reference in its entirety for all purposes. Various modifications and iterations of the shown stapling device are known in the art, having similar features. The circular anastomosis surgical stapling instrument 500a includes a distal stapling head assembly 600 connected by a longitudinally curved support shaft assembly 700 to a proximal actuator handle assembly 800. The stapling instrument includes an anvil assembly or anvil 1000a which is slidable longitudinally relative to the stapling head assembly 600 and mounted on an axially extending moveable shaft 1040. An optional rotatable adjusting knob 820 is provided at the proximal end of the actuator handle assembly 800 for adjusting the spacing between the stapling head assembly 600 and the anvil assembly 1000a. Other approximating means to compress adjacent sections of tissue are known to skilled artisans and can be used. An optional movable indicator 840 is visible through an optional window 850 on top of the handle assembly 800 to indicate the staple height and/or gap between the stapling head assembly 600 and anvil 1000a selected by rotation of the adjusting knob 820. The indicator 840 is movable indicating that the anvil gap is within a desired operating range of the stapling instrument 500a. The position of the indicator 840 also indicates whether the selected staple height is large or small.

A staple actuating lever 860 is pivotally mounted on the actuator handle assembly 800 for driving the surgical staples from the stapling head assembly 600 when the anvil assembly 1000a is closed to provide the desired staple height. A pivotal latching member 880 is mounted on the handle assembly 800 for locking the staple actuating lever 860 against movement to preclude actuation of the stapling head assembly 600 when the anvil gap is outside of a predetermined range. The stapling head assembly 600 includes a tubular casing 610 as well as a hollow tubular connector 640 at the proximal end of the casing 610 which receives the distal end of the support shaft 700. A ferrule or sleeve 720 overlaps the joint between the tubular connector 640 and the distal end of the support shaft 700. The proximal end of the support shaft 700 is received by a tubular extension 740 at the distal end of the actuator handle assembly 800. A ferrule or sleeve 760 overlaps the joint between the proximal end of the support shaft 700 and the distal end of the tubular extension 740. The movable indicator 840 is visible through a window 850 on top of the handle assembly 800 to indicate the staple height selected by rotation of the adjusting knob 820.

Other versions and modifications of the circular surgical stapler are known to a skilled artisan. There are typically at least two and frequently more concentric stapling lines or concentric circular rows of staples-containing slots surrounding shaft 1040, with staples in each row typically staggered or offset relative to the staples in the adjacent row, to improve the sealing and prevent leakage along the stapling line.

According to one aspect of the present invention, locally pre-cooling tissue immediately prior to stapling is beneficial for better surgical outcomes. Circular stapler has a cooled zone that enables cooling of tissue after the stapler is positioned on/in the tissue, immediately prior to stapling. Cooled zone is located in or on the anvil and/or stapling head in proximity to the tissue facing surfaces of anvil and/or stapling head or and is represented by the below described coolant reservoirs or compartments containing pre-cooled coolants or instant coolant; coolant reservoirs connected to recirculating coolants; electrically cooled Peltier elements; compressed gas cooled throttling orifices connected to gas conduits and to sources of compressed gas; heat pipe transferring thermal energy between stapling head and/or anvil and a cooling zone in stapler handle. Cooled zone is configured to transfer thermal cooling energy to the tissue facing surfaces so that tissues in contact with these tissue facing surfaces are pre-cooled prior to stapling.

Figure 2:
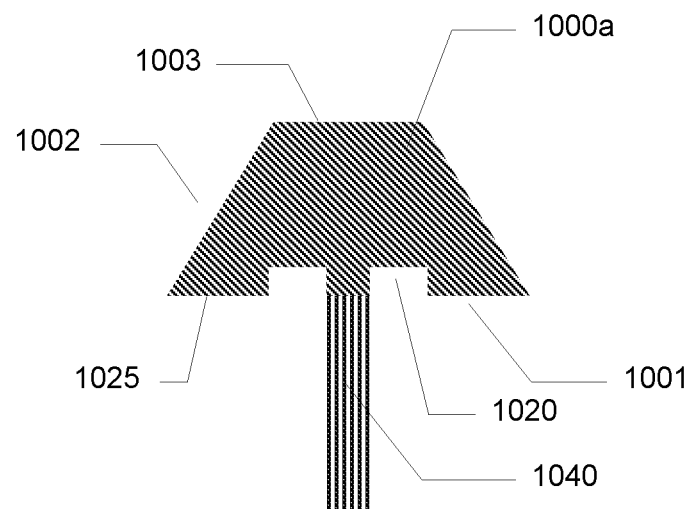
FIG. 2 shows schematic cross-sectional views of a typical anvil.

Turning now to FIG. 2, a schematic cross-sectional view of anvil 1000a is shown as known in the art. Anvil 1000a is shown having distal end or upper portion 1003, sidewall 1002, tissue facing end or staples facing surface 1001, with a staple bending zone 1025 at a periphery of staples facing surface 1001 opposing staples 110 rows (not shown); moveable shaft 1040 connected to anvil 1000a, and circular or concentric knife abutting zone or circular knife recess 1020.

Figure 3A:
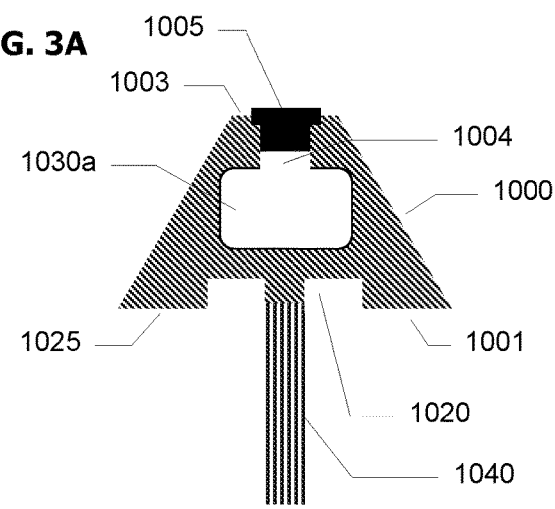
FIGS. 3A-3D show schematic cross-sectional views of anvils of the present invention.

Turning now to FIGS. 3A-3D, schematic cross-sectional views of anvil 1000 of present invention are shown. FIG. 3A shows an embodiment of anvil 1000 having an internal cylindrical coolant chamber or coolant reservoir or coolant compartment 1030a inside, filled with a coolant. An optional fill port 1004 shown in FIG. 3A only, connects compartment 1030a to outside of anvil 1000, terminating on upper portion 1003 and capped with a cap 1005. Coolant compartment 1030a can be of any shape, including generally cylindrical (as shown), spherical, ellipsoidal, toroidal, cuboidal, pyramidal, cone-shaped, truncated cone or frusto-conical shaped, etc. Optionally (not shown) cap 1005 could be as wide as upper portion 1003 and comprise a screw-on component.

Figure 3B:
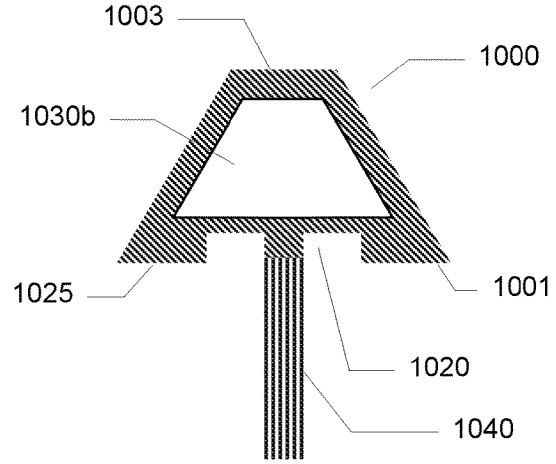

FIG. 3B shows an embodiment like one shown in FIG. 3A, but having wider and expanded coolant compartment 1030b of generally frusto-conical shape which is configured to take as much as possible of the available space inside anvil 1000.

Figure 3C:
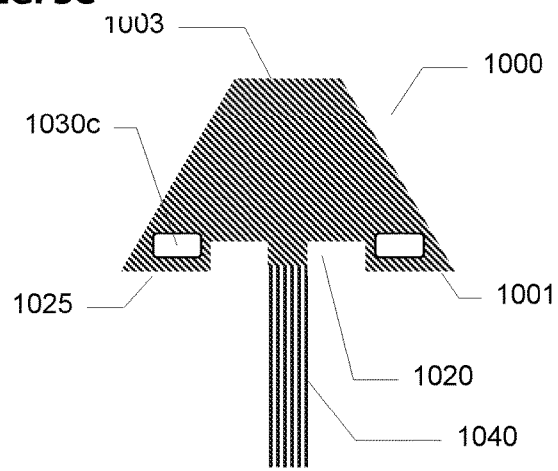

FIG. 3C shows an embodiment like one shown in FIG. 3A, but having a ring-shaped or toroidal configuration of coolant compartment 1030c inside anvil 1000, with coolant compartment 1030c positioned near staple bending zone 1025 and staples facing surface 1001.

Figure 3D:
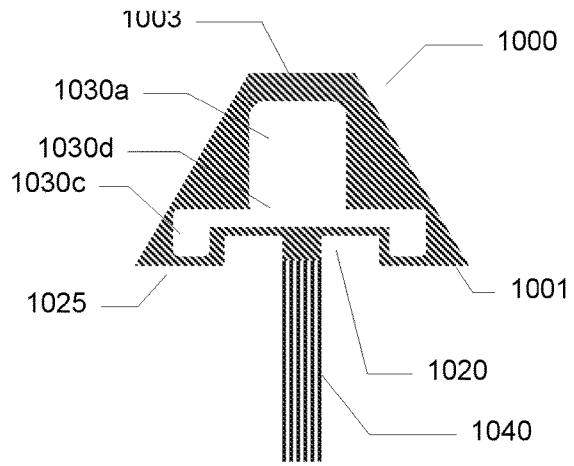

FIG. 3D shows an embodiment like embodiments of FIGS. 3A-3C, with coolant compartment 1030d combining elements of toroidal configuration 1030c and elements of cylindrical configuration 1030a.

Figure 4A:
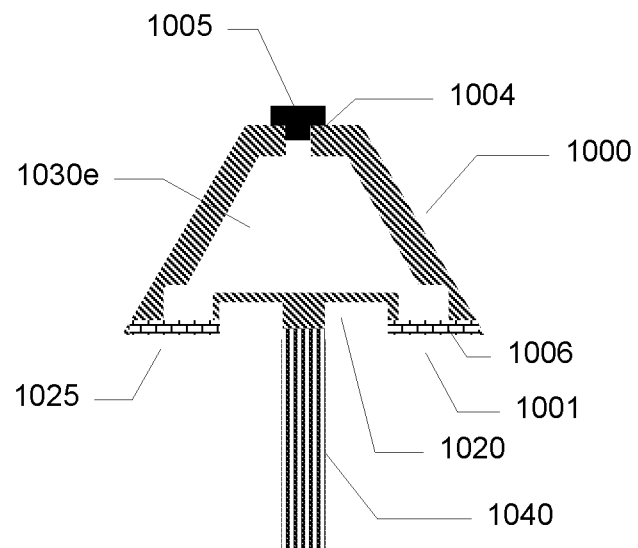
FIGS. 4A-4B show schematic cross-sectional views of anvils of the present invention.

Turning now to FIG. 4A, an embodiment is shown that like embodiments of FIG. 3, with coolant compartment 1030e combining elements of toroidal configuration 1030c and elements of frusto-conical configuration 1030b, with optional fill port 1004 capped with a cap 1005 also shown. An optional thermally conductive zone 1006 extends from being in contact with coolant compartment 1030e towards staple bending zone 1025 and/or staples facing surface 1001. Optional thermally conductive zone 1006 is forming staple bending zone 1025 and/or staples facing surface 1001 and is made of any highly thermally conductive metal or alloy, including but not limited to copper or copper based alloy, aluminum or aluminum alloy, brass, and similar, with highly thermally conductive metal or alloy having thermal conductivity in excess of thermal conductivity of stainless steel, such as at least double the thermal conductivity of stainless steel, more preferably five times higher than thermal conductivity of stainless steel. This configuration is facilitating heat transfer and cooling of tissues adjacent to and in contact with staple bending zone 1025 and/over staples facing surface 1001 and prevents heat transfer and cooling of tissues not adjacent and not in contact with staple bending zone 1025 and/or staples facing surface 1001.

Figure 4B:
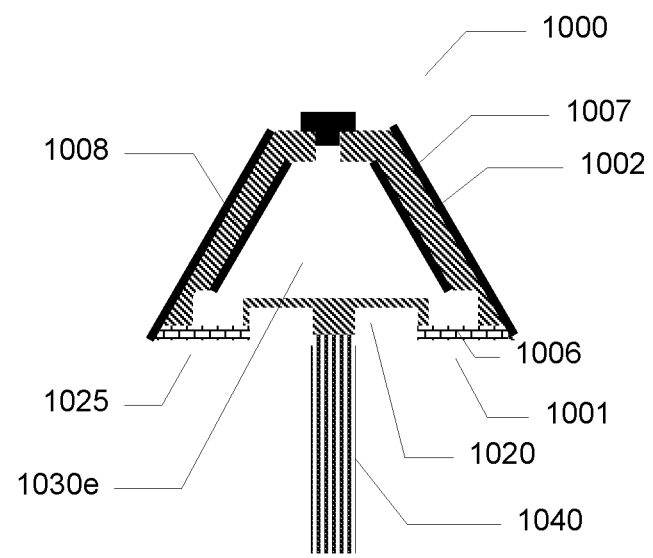

FIG. 4B shows an embodiment like the embodiment of FIG. 4A, further having an optional thermally insulating external coating 1007 on external surfaces of anvil 1000, such as on sidewall 1002 but not covering staple bending zone 1025 and/or staples facing surface 1001, regardless of whether optional thermally conductive zone 1006 is present (as shown) or not. Also shown is optional thermally insulating internal coating 1008 on internal surfaces of coolant compartment 1030e, not covering portions of coolant compartment 1030e adjacent to staple bending zone 1025 and/over staples facing surface 1001, regardless of whether optional thermally conductive zone 1006 is present (as shown) or not. This configuration is facilitating heat transfer and cooling of tissues adjacent to and in contact with staple bending zone 1025 and/or staples facing surface 1001 and prevents heat transfer and cooling of tissues not adjacent and not in contact with staple bending zone 1025 and/or staples facing surface 1001.

In all embodiments, thermal energy of coolant contained in compartments 1030 is used to facilitate heat transfer from tissue to coolant and to cool tissue immediately prior to stapling.

Figure 5A:
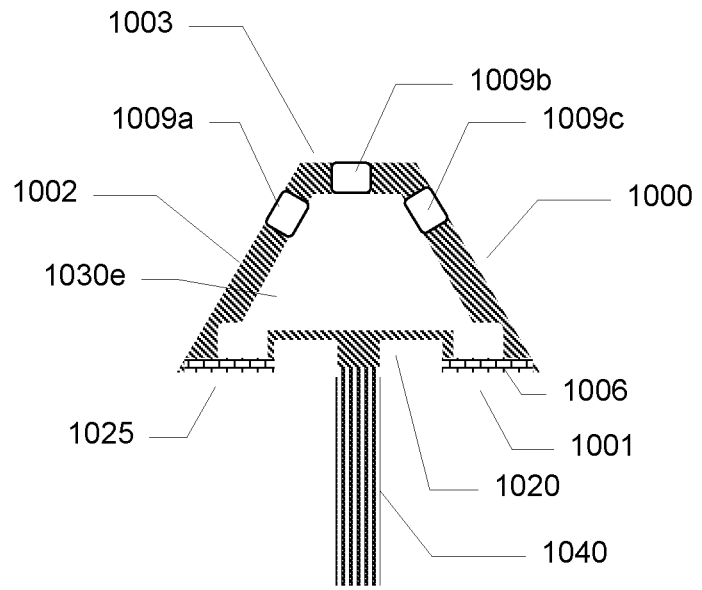
FIGS. 5A-5C show schematic cross-sectional views of anvils of the present invention.

Referring to FIG. 5A, at least one or more optional windows 1009a, 1009b, 1009c are installed on upper portion 1003 and/or sidewall 1002, the windows can then be utilized to detect two-phase ice/water mixture presence in coolant compartments 1030 indicating temperature of 0° C. in case of pure water and another temperature in case of coolant comprising mixtures, such as lower temperature for salt/water mixtures.

Figure 5B:
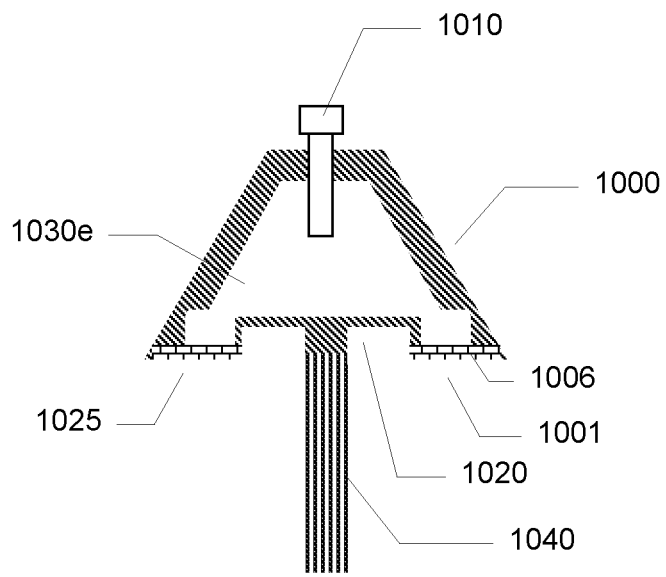

Referring to FIG. 5B, an optional temperature probe, sensor, or indicator 1010 can be installed on anvil 1000, such as on upper portion 1003, including electronic indicator, color change indicator, bi-metallic temperature indicator, etc. Temperature probe 1010 can also comprise a port for measuring electric output from a thermocouple, thermistor, and similar sensor installed inside compartments 1030.

Figure 5C:
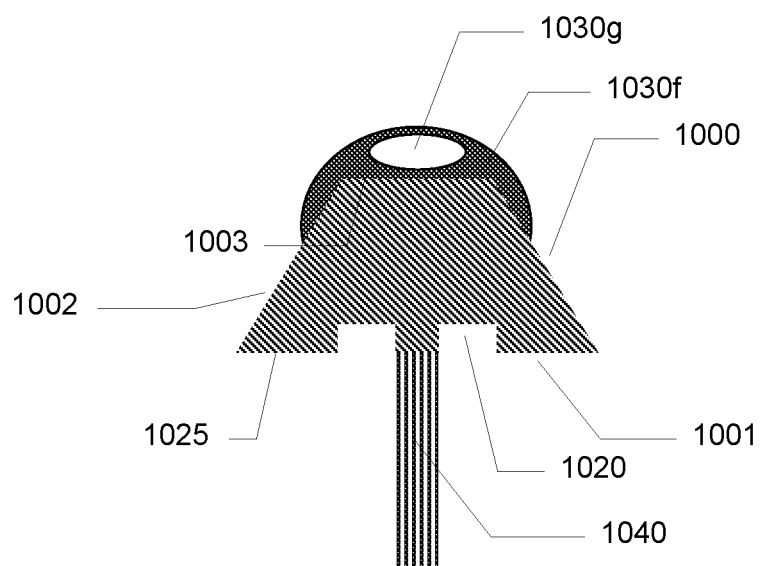

Referring to FIG. 5C, a simplified cross-sectional view of an embodiment of anvil 1000 of the present invention is shown, with anvil 1000 having an external coolant chamber or coolant reservoir or coolant compartment 1030f which is externally attached to anvil 1000 and installed on upper portion 1003 and/or sidewall 1002. External cooling compartment 1030f can be optionally fixated by pressure fit, tongue and groove fastening, or via any other attachment fasteners (not shown) located in on upper portion 1003 and/or on side wall 1002. In all cases fasteners enable snap-on rapid attachment and removal of coolant compartment 1030f. Attachable and detachable external coolant compartment 1030f comprises in a preferred embodiment a hollow body with an internal cavity 1030g (as shown ion FIG. 5C) that is filled with coolant. In an alternative embodiment (not shown), external coolant compartment 1031f comprises solid non-hollow body that is made of metal.

According to at least some embodiments of the present invention, coolant reservoirs or compartments 1030 contain coolant, preferably a fluid coolant, that preferably has high heat capacity or thermal capacity and thus can store substantial amounts of cooling energy which is then transferred to tissue for tissue cooling immediately prior to stapling. High heat capacity or thermal capacity materials are characterized by high specific heat capacity, with preferred coolant being water, normal saline, or any aqueous solution. Pure water or water containing minor amounts of dissolved compounds can be used as a coolant, water having very high heat capacitance of about 4 J/g/K. Salt-water mixtures can be utilized for temperatures lower than 0° C.

Compartments 1030 can contain from 1 to 20 g of water, such as 1, 2, 3, 4, 5, 6, 7 g. Providing for instance 5 g of water inside compartments 1030 would result in the following cooling energy production. With water inside compartments 1030 initially at +5° C. heating to +10° C. during tissue cooling, would absorb amount of energy from the surrounding area, which includes tissue, equal to about 5 g*5° C.*4=100 J.

Water is also characterized by very high enthalpy of fusion (latent heat of fusion), which is the amount of energy consumed or released during phase transition such as melting, with water having specific heat of fusion of about 334 J/g. In one embodiment, water inside coolant reservoirs or compartments 1030 is initially frozen i.e. converted into ice. The amount of energy absorbed from the surrounding area as the ice is melting at 0° C., will be equal to about 5 g*334=1670 J. If the melted water is then heated to +10° C., the additional amount of energy consumed and absorbed from the surrounding area, which includes tissue, is equal to about 5 g*10° C.*4=200 J. Considering that the weight of target tissue is comparable to from 1 to 5 g, it is expected that the target tissue can be substantially cooled below normal tissue temperature of 36.6° C., such as cooled to +3 . . . +15° C., such as cooled to temperature of about +5, +7, +10° C. during brief contact with anvil 1000 immediately prior to stapling, such as within 5-300 seconds, more preferably 10-120 s, such as 10, 20, 30, 60 s.

It is preferred that there is no freezing of tissue on contact with hypothermic or cooled anvils 1000 of the present invention, and no permanent tissue damage. Accordingly, the temperature of the surfaces in contact with tissue is configured to be below tissue temperature, such as from about −10° C. to about +10° C. or even up to 20° C., such as −5, −3, 0, +3, +5° C., +10° C. For purposes of this disclosure, the term "hypothermic" means to effectively lower the temperature of tissue relative to normal body temperature in the immediate vicinity of the device by some artificial means as described further herein.

In some embodiments, coolant fluid comprises a material or a mixture having freezing point higher or lower than 0° C. In one embodiment, water-salt mixtures, water alcohol mixtures, and water-glycerol mixtures are used, all having freezing point lower than 0° C. In one embodiment, a mixture of water with glycerol is used that has the freezing point above 0° C., with concentration glycerol (% weight) of between 90% and 98.3% resulting in freezing points between −1.7° C. and +13° C., particularly concentrations from 93% to 95% of glycerol are useful for creating melting or freezing points of mixtures above 0° C. but below +8° C.

Cooling of tissue is intended not to result in any permanent damage of tissue or freezing of tissue. While cooled compartments can be below 0° C., when tissue itself is cooled below 0° C., it is performed only transiently and for brief periods of time, such as 1 s, 3 s, 10 s, 20 s. Similarly, when tissue is cooled to low temperature such as 5° C., it is performed also only transiently and for brief periods of time, such as 3 s, 10 s, 20 s, 60 s.

Figure 6A:
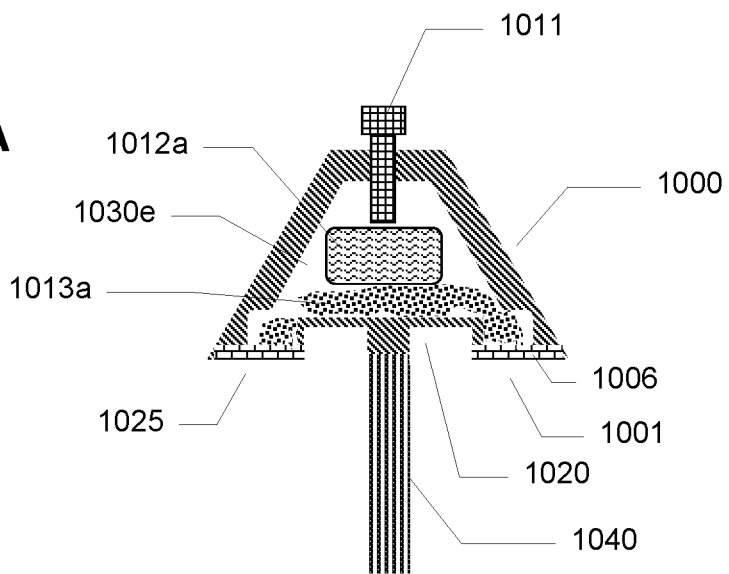
FIGS. 6A-6B show schematic cross-sectional views of anvils of the present invention.

In some embodiments, instant cooling is provided inside compartments 1030 using endothermic reactions of dissolving salt in water. The salts used can be ammonium nitrate, calcium ammonium nitrate, urea, or similar, whereby the salts are separated form water by a frangible membrane. Referring to FIG. 6A, in one embodiment, salts 1013a having high endothermic enthalpy of dissolution are filled into compartment 1030e, with frangible bag 1012a containing water also placed inside compartment 1030e. An actuating lever 1011 configured to be accessible from outside of anvil 1000 and adapted to reach frangible bag inside compartment 1030e is provided. Actuation of lever 1011 to break frangible bag 1012a releases water from bag 1012a resulting in mixing of salts with water dissolving the salts in an endothermic reaction and instant cooling of anvil 1000.

Figure 6B:
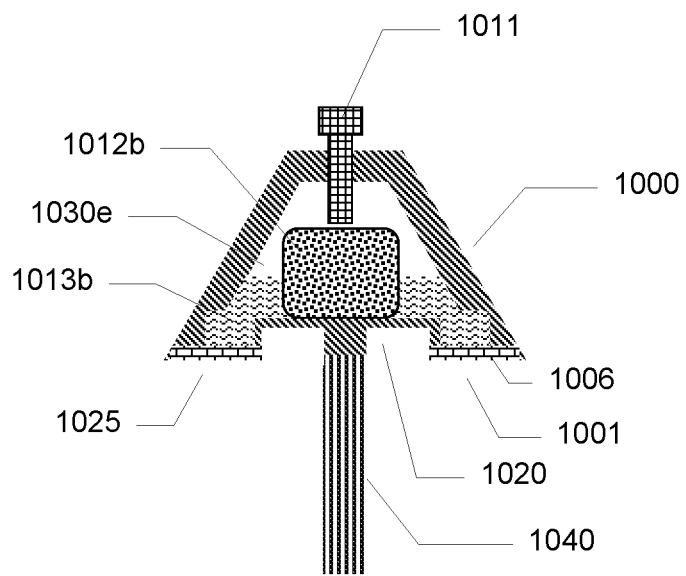

Referring to FIG. 6B, in another embodiment, salts are enclosed in a frangible bag 1012b placed inside compartment 1030 filled with water 1013b. Actuation of lever 1011 to break frangible bag 1012b releases salts from bag 1012b resulting in mixing of salts with water dissolving the salts in an endothermic reaction and instant cooling of anvil 1000.

Instant coolant mixture can be activated for producing cooling prior to any contact with tissues being joined, or after installing stapler 500 components into tissues being joined, or immediately prior to stapling. In addition, the activation of cooling can be the connection of the trocar to the anvil. In this embodiment (not shown), lever 1011 is associated with shaft 1040 and upon connecting shaft 1040 to stapling head 600, lever 1011 pushes into frangible bag 1012a or 1012b thus initiating cooling automatically upon connection of anvil 1000 to stapling head 600.

Figure 7:
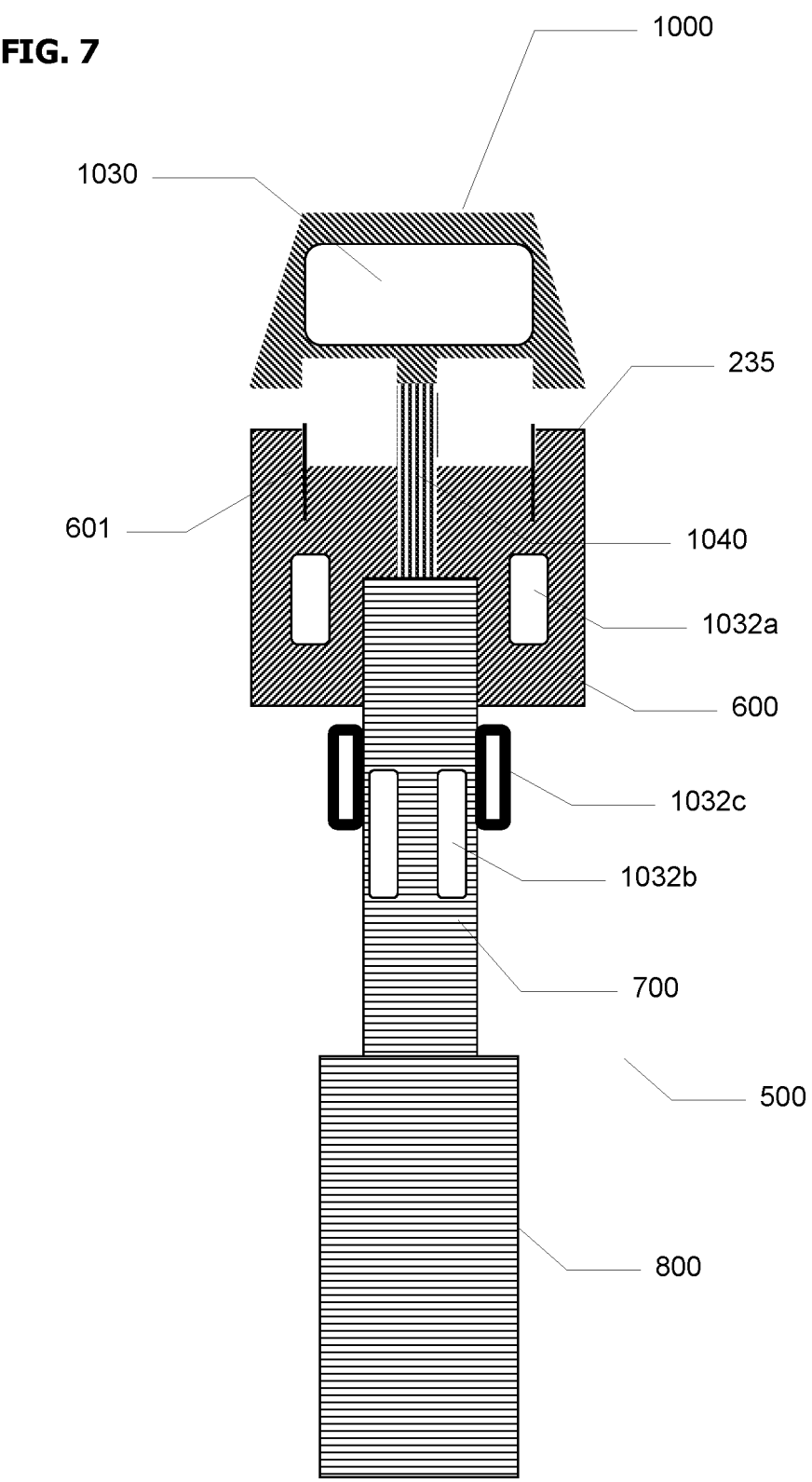
FIGS. 7-10 show schematic cross-sectional views of assembled staplers of the present invention.

Referring now to FIG. 7, a schematic cross-sectional view of an embodiment of an assembled circular stapler 500 is presented. Anvil 1000 is shown connected to stapling head 600 via moveable shaft 1040. Stapling head 600 is shown supported on support shaft assembly 700 which is terminating in handle 800. For simplification, the mechanism of staples (not shown) deployment and mechanism of deploying tissue cutting circular or concentric knife 601 are not shown. Anvil 1000 is shown having coolant compartment 1030.

Similarly to the inventive embodiments of anvil 1000 presented above, stapling head 600 in some embodiments has optional coolant reservoirs or coolant compartments, such as shown toroidal shaped coolant reservoir or coolant compartment 1032a. In another embodiment, optional coolant compartment is located within support shaft assembly 700, such as shown toroidal shaped coolant compartment 1032b. In yet another embodiment, cooling compartment is positioned externally on support shaft assembly 700, such as shown toroidal shaped coolant compartment 1032c. In some embodiments, compartments 1032a and 1032b are interconnected (nor shown) or are represented by one compartment (not shown).

In some embodiments (not shown), there is provided an optional thermally conductive zone like thermally conductive zone 1006 which extends from coolant compartment 1032 to staple-deploying tissue facing surfaces 235 of stapling head 600.

In some embodiments (not shown), at least one optional window, like windows 1009a, 1009b, 1009c is installed on stapling head 600 and/or on support shaft assembly 700, utilized to detect two-phase ice/water mixture presence in coolant compartments 1032. In some embodiments (not shown), at an optional temperature probe, sensor, or temperature indicator like indicator 1010 can be installed on stapling head 600 and/or on support shaft assembly 700.

In some embodiments (not shown), instant cooling is provided inside compartments 1032 using endothermic reactions of dissolving salt in water, like embodiments of FIGS. 6A, 6B, with an actuating lever like actuating lever 1011 configured to be accessible and adapted to reach frangible bag inside compartment 1032.

Figure 8:
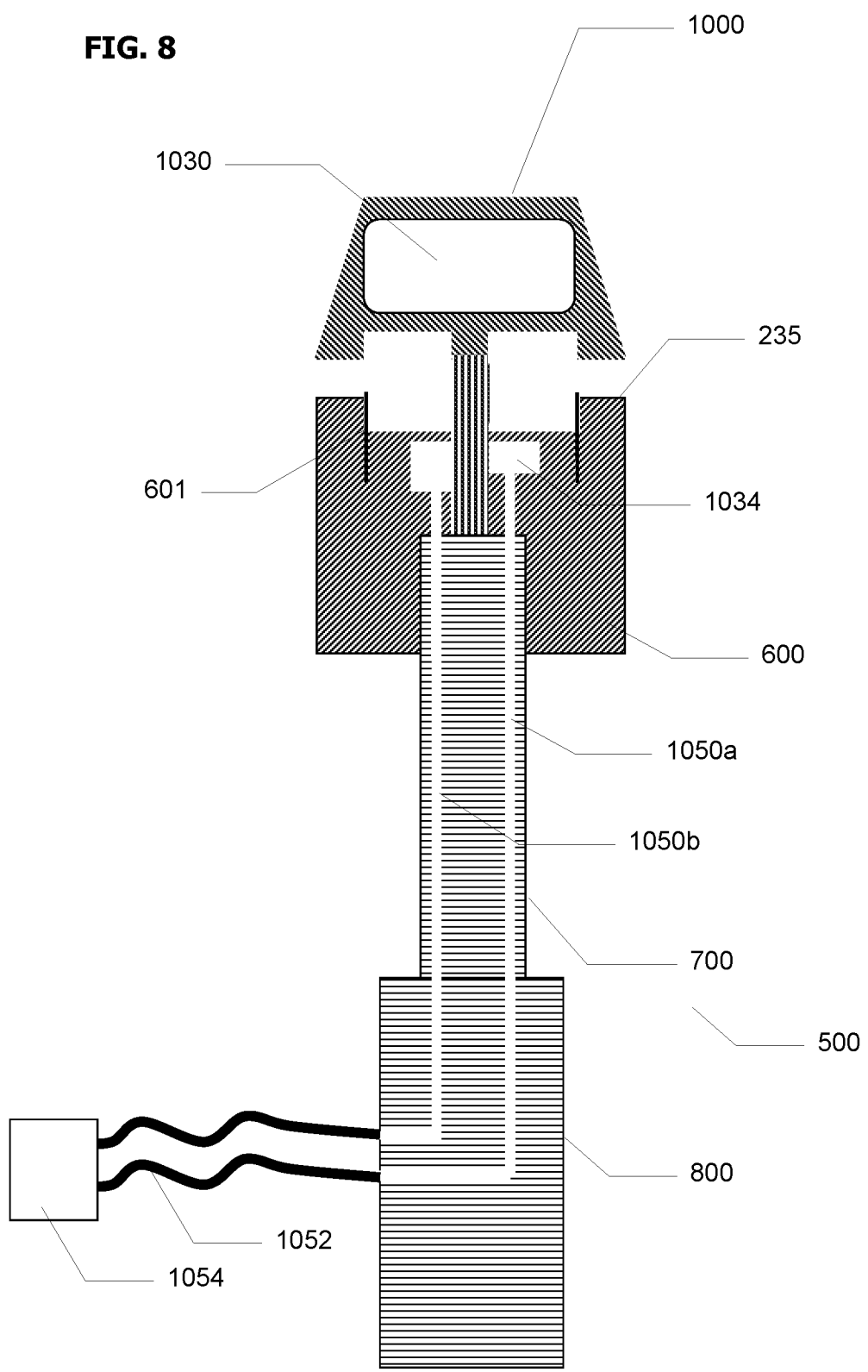

Referring now to FIG. 8, in some embodiments, there is provided in stapling head 600 a recirculation coolant reservoir or cooling compartment 1034, into which chilled coolant is supplied via supply channel 1050a and drain channel 1050b, such channels terminating on handle 800 and connected to supply/drain lines 1052 which are connected to a pump and chiller 1054 adapted to supply cooled fluid coolant. Compartment 1034 can be positioned closer to stapling area than shown in FIG. 8. Pump and chiller 1054 can be positioned outside of stapler 500 (as shown) or inside (not shown). In operation, recirculation of cooled fluid coolant lowers the temperature of stapling head 600 to a desired temperature from about 0° C. to about 10° C. such as 5° C. Recirculation can continue during stapling operation or can be stopped prior to stapling or prior to insertion into tubular tissue. Coolant reservoir or cooling compartment 1034 can comprise a chamber or a tubular coil.

Figure 9:
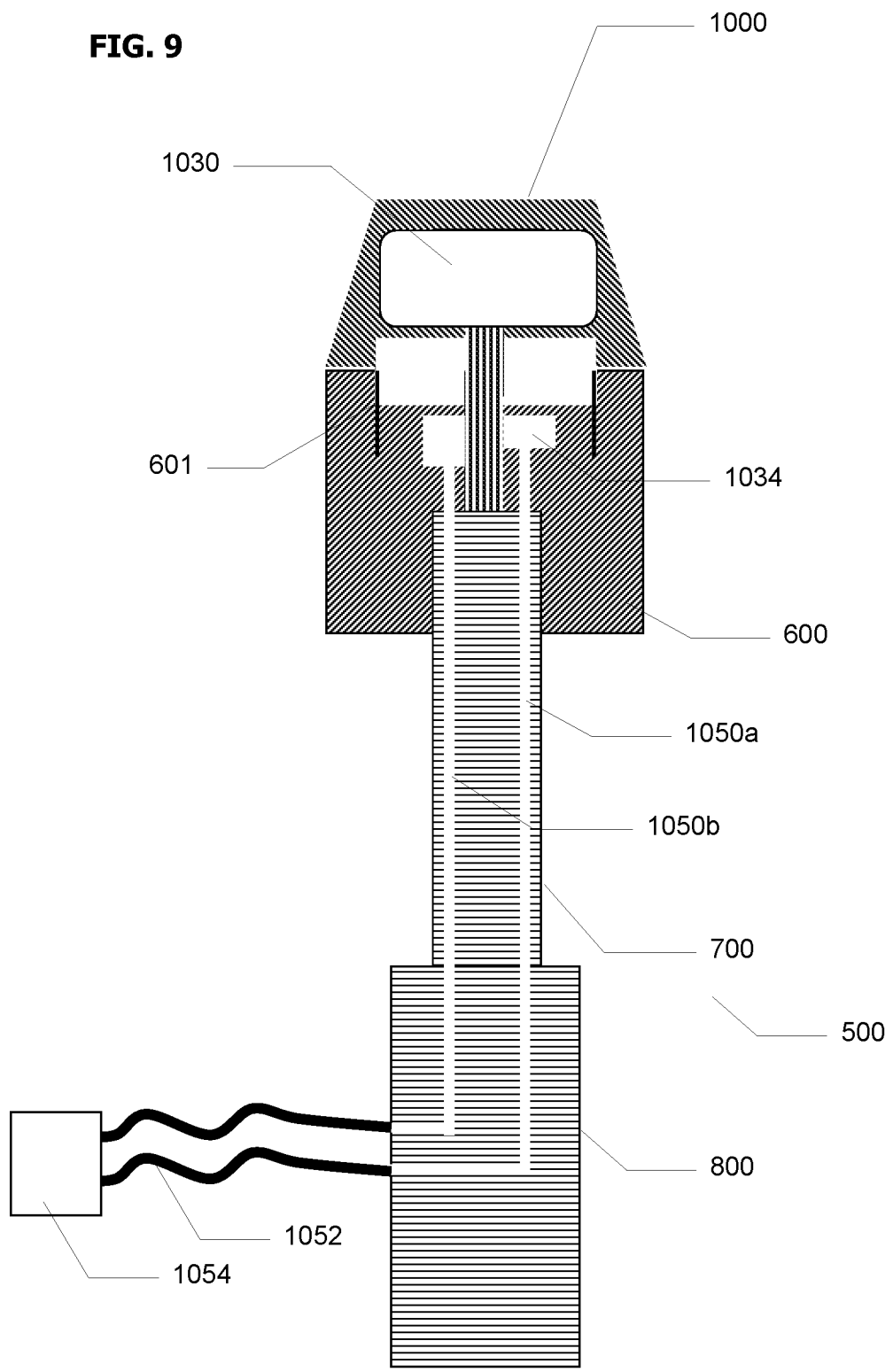

Optionally, prior to installation of anvil 1000 in tubular tissue prior to stapling, anvil 1000 is brought into contact with stapling head 600 as shown in FIG. 9 and pre-cooled using conductive heat transfer from stapling head 600 for several minutes, such as 5-60 minutes. As the anvil will be in contact with tissue first, a separate cooling via the anvil can be implemented.

In an alternative embodiment, there is provided the cooled zone comprising a Peltier element (not shown) positioned with its cold plate proximal to tissue facing surfaces 235 of stapling head 600 and or to tissue facing end or staples facing surface 1001 of anvil 1000. Supplying electric energy to the Peltier element results in cooling of the tissue facing surfaces.

Figure 10:
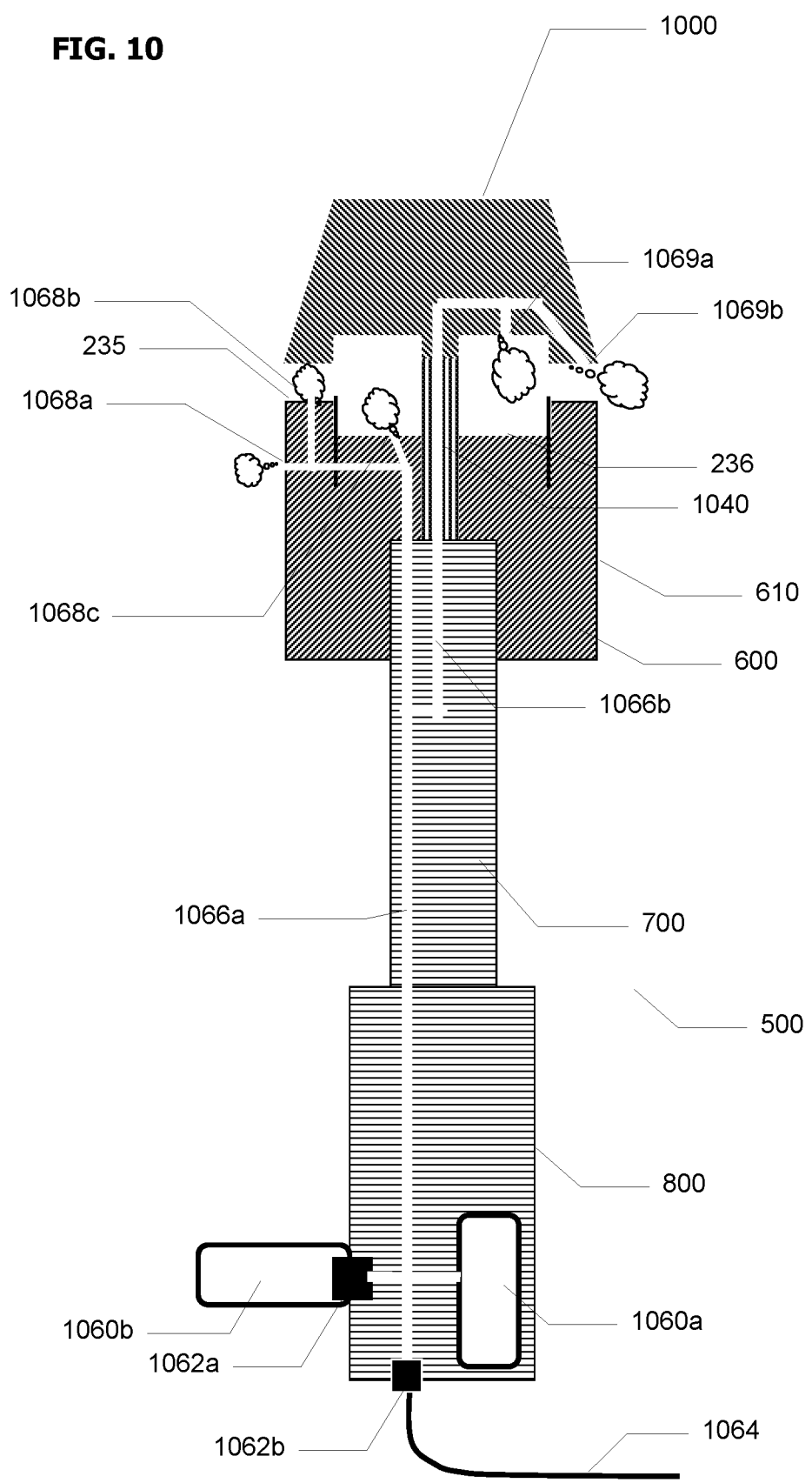

According to another embodiment of the present invention, pre-cooling of anvil 1000 and or stapling head 600 is performed by a throttling process or Joule-Thomson process or adiabatic expansion cooling, whereby compressed gas can expand and exit into the surrounding through a throttling orifice, valve, or porous permeable plug from a higher to a lower pressure. Referring to FIG. 10, source of compressed gas, such as air, CO2, nitrogen, or similar, is provided. Source can be a balloon with compressed gas, such as balloon 1060a located inside handle 800, balloon 1060b located proximal to handle 800 and connected to it via gas port 1062a, or source of compressed gas can be (not shown) distal to handle 800 and connected to a gas port 1062b via gas supply line 1064.

A gas conduit line 1066*a* is configured to carry compressed gas from handle 800 area towards stapling head 600, terminating at one or more throttling orifices, located as shown, with throttling orifices 1068*a* located anywhere on tubular casing 610, throttling orifices 1068*b* located on staple-deploying tissue facing surfaces 235, and/or throttling orifices 1068*c* located inside circular knife well 236.

A gas conduit line 1066*b* is configured, additionally or alternatively, to carry compressed gas from handle 800 area towards anvil 1000, terminating at one or more throttling orifices, located as shown, with throttling orifices 1069*a* located in circular knife recess 1020 or throttling orifices 1069*b* located on staples facing surface 1001 or on staple bending zone 1025.

Compressed gas released from throttling orifices 1068, 1069 is schematically shown in FIG. 10 by a gas cloud symbol. The diameters of throttling orifices 1068, 1069 are from about 20 to about 2000 microns, such as 30, 50, 100, 200, 300, 500, 800, 1000, 1500 microns. For the circular anastomosis, the gas should be re-routed from the entrance and cannot be allowed to be released in the GI system. The cooling is preformed prior to inserting the stapler into the tubular tissues.

According to an alternative embodiment of the present invention, the cooled zone comprises a heat pipe (not shown) which is utilized to transfer thermal energy between stapling head 600 and/or anvil 1000 and a cooling zone or cooling reservoir in handle 800. Heat pipes are known in the art and represent a heat-transfer device that utilizes thermal conductivity and phase transition to efficiently manage the transfer of heat over long distances. At the warm/hot interface of a heat pipe, a liquid in contact with a thermally conductive solid surface turns into a vapor by absorbing heat from that surface. The vapor then travels along the heat pipe to the cold interface and condenses back into a liquid— releasing the latent heat. The liquid then returns to the hot interface through either capillary action, gravity, or both, and the cycle repeats. In the instant application, heat pipes operating at room temperature are envisioned, particularly based on ammonia, alcohol as the working fluid, and using copper or aluminum alloys as pipe materials.

In operation of all embodiments, the cooled surfaces which are in contact with tissues are maintained at above tissue freezing temperature, such as above −3, −2, −1, 0° C., most preferably above 0° C., such as at 0, +1, +2, +4, +5, +6, +8, +10° C., to avoid freezing of tissue to the stapler and to avoid thermal injury to tissue. In some embodiments, cooled zone is at temperature below tissue freezing temperature, such as at −10° C., but upon contact with tissue and heat exchange between cooled zone and tissue, temperature rapidly raises to above tissue freezing such as above 0° C., such as reaching 0, 3, 5° C.

Figure 11:
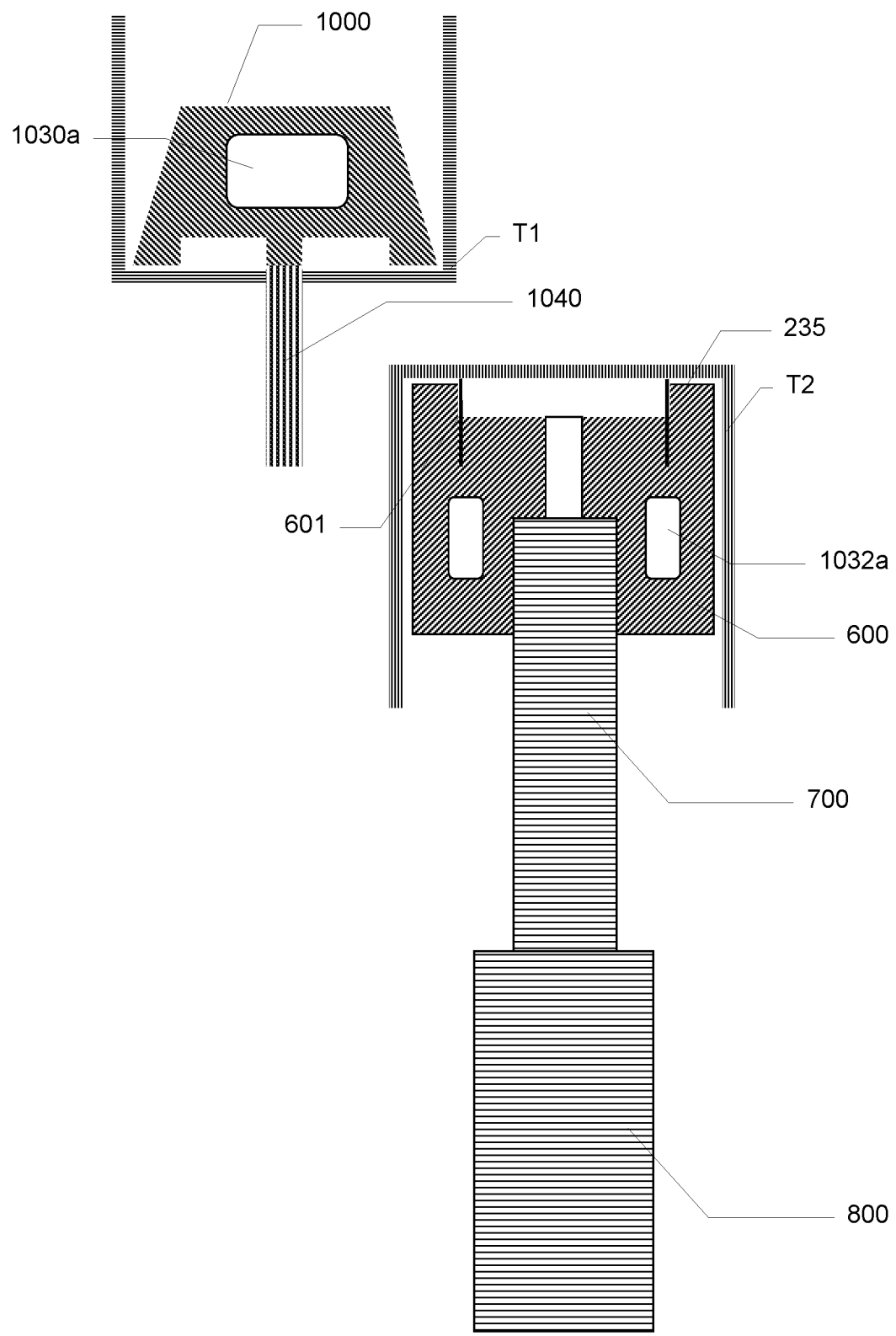
FIG. 11 shows schematic cross-sectional view of components of stapler of the present invention in operation.

Referring now to FIG. 11, a schematic cross-sectional view of anvil 1000 and stapling head 600 on support shaft assembly 700 with handle 800 prior to forming assembled circular stapler 500 prior to anastomotically joining tissues T1 and T2 is presented. Anvil 1000 is shown disposed within tubular tissue T1 and stapling head 600 is shown disposed within tubular tissue T2 and supported on support shaft assembly 700. The positions shown are prior to connecting shaft 1040 to stapling head 600.

For simplification, the mechanism of staples deployment and mechanism of deploying tissue cutting circular or concentric knife 601 are not shown. For simplification, anvil 1000 is shown as embodiment like the embodiment of FIG. 3A having coolant compartment 1030*a*. However, any of the above embodiments of anvil 1000 and cooling elements of anvil 1000 can be utilized, including coolant compartments 1030 in anvil or externally attached to anvil; containing coolant and/or frozen coolant; instant coolant utilizing endothermic reactions of dissolving salt in water; recirculating coolant; electric cooling embodiments; compressed air cooling embodiments; and heat pipe based cooling embodiments. Similarly, for simplification, stapling head 600 is shown as embodiment like the embodiment of FIG. 7 having coolant compartment 1032*a*. However, any of the above embodiments of stapling head 600 and cooling elements of stapling head 600 can be utilized, including coolant compartments 1032, containing coolant and/or frozen coolant; instant coolant utilizing endothermic reactions of dissolving salt in water; recirculating coolant; electric cooling embodiments; compressed air cooling embodiments; and heat pipe based cooling embodiments.

All the above elements facilitating cooling of anvil and/or stapling head are activated prior to positioning anvil 1000 and stapling head 600 into tubular tissues T1 and T2, except for instant coolant, recirculating coolant; and electric cooling elements which can be activated before OR after positioning anvil 1000 and stapling head 600 into tubular tissues T1 and T2.

As can be appreciated from FIG. 11, once tubular tissues T1 and T2 are positioned on respectively anvil 1000 and stapling head 600, tubular tissues T1 and T2 are being cooled by conductive heat transfer, especially in the areas of contact with anvil 1000 and stapling head 600. Such cooling can be performed for any convenient period as preparations for stapling are made, preferably for at least 20 s, such as 30, 60, 120, 300, 600 s or more.

Figure 12:
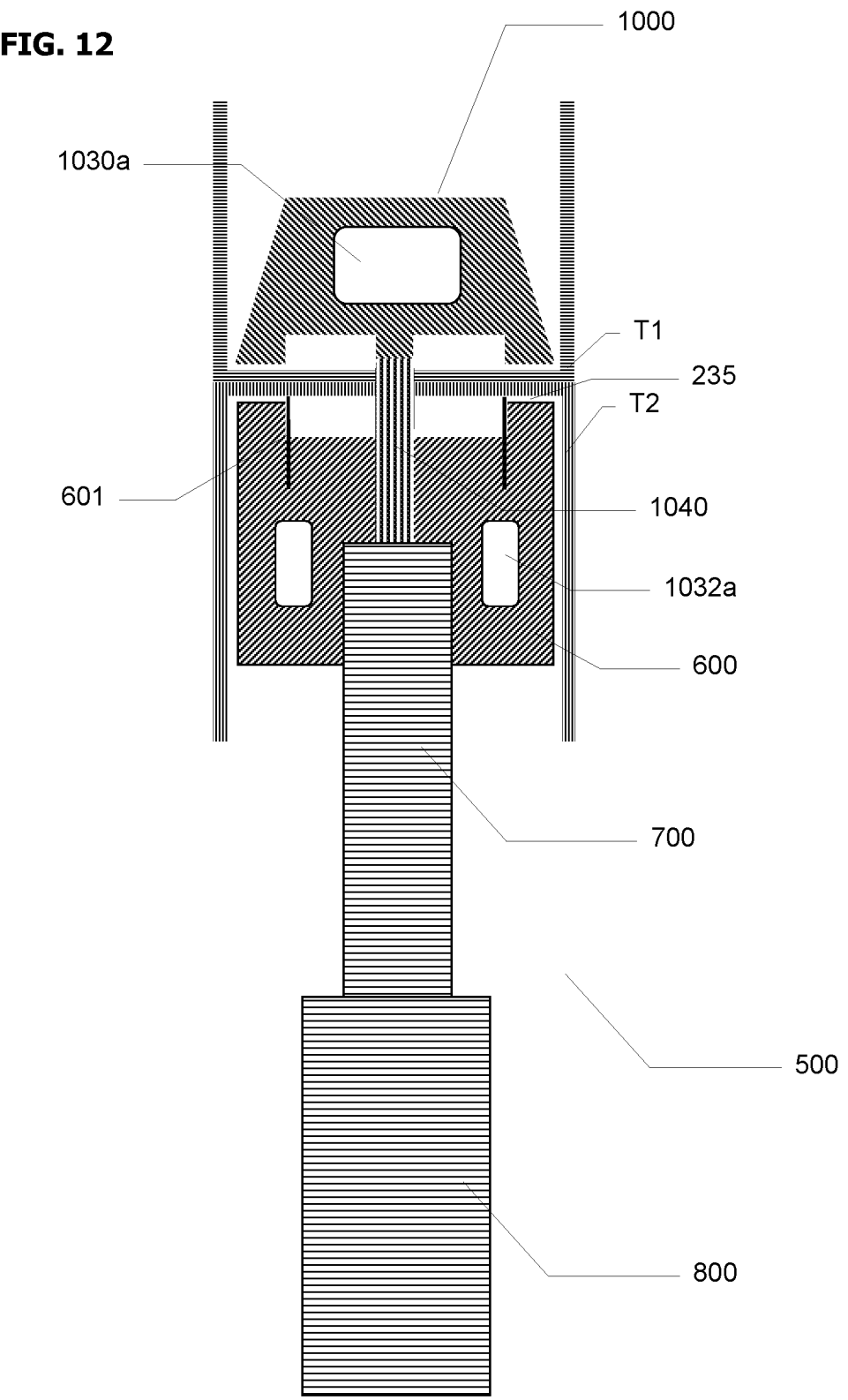
FIGS. 12-13 show schematic cross-sectional views of assembled stapler of the present invention in operation.

Referring now to FIG. 12, a schematic cross-sectional view of an assembled circular stapler 500 prior to anastomotically joining tissues T1 and T2 is presented. Anvil 1000 is shown disposed within tubular tissue T1 and connected to stapling head 600 via moveable shaft 1040. Stapling head 600 is shown disposed within tubular tissue T2 and supported on support shaft assembly 700. FIG. 12 shows anvil 1000 and stapling head 600 approximated, compressing tissue T1 and T2 between them. According to the present invention, if tubular tissues T1 and T2 had sufficient time to pre-cool prior to approximation in stapler 500 as shown, stapling can be performed immediately after approximation. In some cases, however, it will be desirable to further cool tissues which are about to be stapled and cut, with cooling efficiency increased due to approximation and compression of tubular tissues T1 and T2 between anvil 1000 and stapling head 600 and better heat transfer due to compression. Also, compression will result in decreased blood perfusion and thus will further facilitate cooling of compressed tissue. Thus, in some embodiments, after performing tissue compression, stapling is not performed for a period ranging from about 10 s to about 300 s, such as 10, 30, 60, 120 s during which time cooling of tissues by conductive heat transfer is performed. Further, immediately before or immediately after approximating tissues T1 and T2 as shown in FIG. 12, instant cooling can be activated if it was not activated prior.

All the above elements facilitating cooling of anvil and/or stapling head are acting prior to position shown in FIG. 12 with anvil 1000 and stapling head 600 interconnected via shaft 1040 and tubular tissues T1 and T2 compression therebetween, except for instant coolant, recirculating coolant; and electric cooling elements which can be activated before OR after compressing tissues T1 and T2.

After compressed tissues T1, T2 are substantially cooled, for instance brought to temperatures below body temperature of 36.6° C., such as to temperatures from about 3° C. to about 20° C., such as 5, 10, 15° C., stapling is actuated, staples (not shown) deploy from stapling head 600 and join tissues T1 and T2 while simultaneously removing excess tissue cutout or "donut" with circular knife 601.

Figure 13:
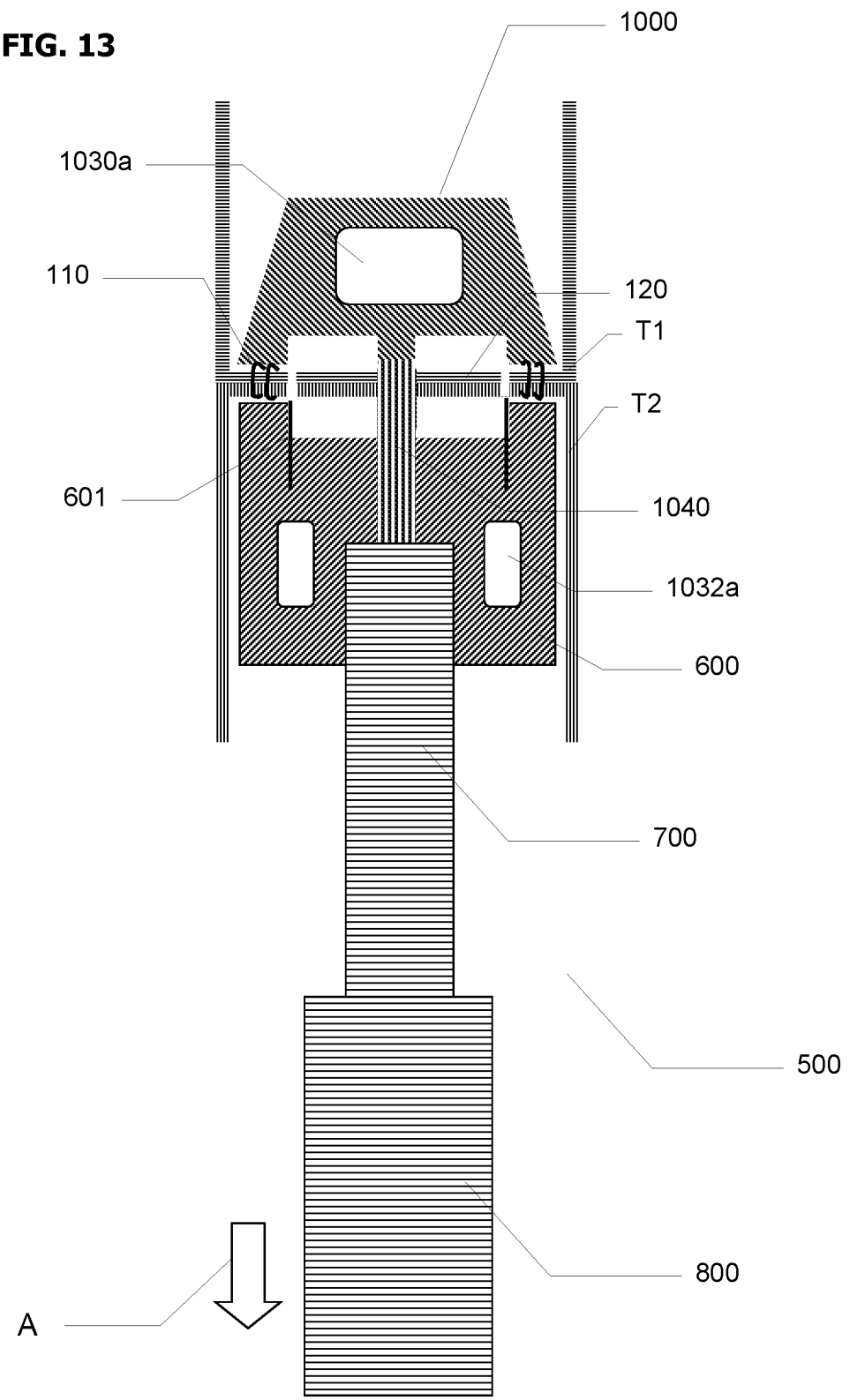

Referring now to FIG. 13, the configuration of embodiment of FIG. 12 is shown after actuating stapling instrument 500, i.e. after staples 110 fired thus establishing a stapled joint between tissues T1 and T2 with staples 110 concentrically arranged in one or more concentric rows around tissue donut or cut-out 120 which is formed by deploying and then retracting tissue cutting circular or concentric knife 601.

After deploying staples 110 and cutting out tissue cutout 120 thus establishing the anastomotic joint, circular stapler 500 is withdrawn in the direction of arrow A. Advantageously, areas of cut and stapled tissues T1 and T2 are beneficially protected from excessive injury by pre-cooling these areas.

According to one embodiment of the present invention, the sequence of using or operating hypothermic staplers 500 while establishing an anastomotic joint is as follows:
a) Axially inserting anvil 1000 into tubular tissue T1 and closing tissue T1 around anvil 1000;
b) Axially inserting stapling head 600 into tubular tissue T2;
c) Connecting anvil 1000 to stapling head 600 via anvil shaft 1040;
d) Approximating anvil 1000 and stapling head 600 and compressing tubular tissues T1 and T2 between stapling head 600 and anvil 1000;
e) Firing anastomotic stapler 500 and establishing stapled anastomotic joint between tissues T1 and T2; and
f) Withdrawing anastomotic stapler 500 from tissue lumens T1 and T2.

Complete steps of anastomotic surgical procedures, e.g. application of purse string sutures are not listed above, but will be known to skilled artisans. The temperature of cooling zone can be in the ranges of −10 C to +20 C or shift from +20 C to −10 C over a short period of time and does not have to stay constant during contact with tissue. The temperature of tissue can decrease upon contact with hypothermic stapler and/or cooling zone from normal tissue temperature to at least 5 degrees Celsius lower, such as 5, 10, 15, 20, 30, 40° C. lower. In some embodiments, tissue temperature in the areas to be stapled is decreased to reach 0, 5, 10° C.

According to the embodiments of the present invention, cooling related steps are performed as per following sequences:

Coolant in Coolant Compartments Embodiments

Coolant in coolant compartment 1030 in anvil 1000 is pre-cooled or frozen prior to axially inserting anvil into tubular tissue T1 and closing tissue T1 around anvil as outlined in step a) above; and/or Coolant in stapling head 600 compartment 1032 is pre-cooled or frozen prior to axially inserting stapling head into tubular tissue T2 as outlined in step b) above.

Similarly, externally attached cooling chamber 1030*f* is pre-cooled or frozen prior to axially inserting anvil into tubular tissue T1 and closing tissue T1 around anvil as outlined in step a) above.

Instant Coolant Embodiments

Instant cooling in compartments 1030 in anvil 1000 is activated prior to step a) or prior to step c) or prior to step d), or immediately after step d) as outlined above;

Instant cooling in compartments 1032 in stapling head 600 is activated prior to step b) or prior to step c), or prior to step d), or immediately after step d) as outlined above.

Recirculation Cooling Embodiments

Instant cooling in recirculation cooling compartment 1034, is initiated or activated prior to step b) or prior to step c), or prior to step d), or immediately after step d) as outlined above. Instant cooling is effected by recirculation of coolant and it can be stopped after stapling head sufficiently cooled, stopping recirculation prior to step b), or prior to step c), or prior to step d) as outlined above.

The temperature can oscillate in the ranges of −10 C to +20 C or shift from +20 C to −10 C over a short period of time and does not have to stay constant during contact with tissue. Electric cooling can be initiated or activated prior to step b) or prior to step c), or prior to step d), or immediately after step d). Electric cooling is initiated by supplying electric power to Peltier elements. Compressed gas cooling can be initiated or activated prior to step a) and will be stopped prior to step b). Compressed gas cooling is initiated by purging gas through gas conduit line 1066*a* and/or 1066*b* and allowing gas to exit through throttling orifices inside anvil 1000 and/or stapling head 600, such as throttling orifices 1068*a*, 1068*b*, or 1068*c* and/or through throttling orifices 1069*a* or 1069*b*. Cooling utilizing heat pipe heat transfer is initiated with coolant in cooling reservoir in handle 800 is pre-cooled or frozen prior to step a) and/or prior to step b). The volumes of compartments 1030, 1032, 1034 are selected to allow fit inside anvil 1000 and/or stapling head 600, with no interferences with stapling mechanisms, and are from about 1 cm$^3$ to about 20 cm$^3$, more preferably 2 to 10 cm$^3$, such as 2, 3, 5, 8, 10 cm$^3$.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims.

We claim:

1. A hypothermic circular stapling instrument comprising: a circular anvil having an anvil tissue facing surface and an opposite distal end; the circular anvil having a peripheral staple bending zone on said anvil tissue facing surface; a cylindrical stapling head mounted on a support shaft, said stapling head containing a concentric knife and a plurality of deployable staples in concentric arrays within a stapling head tissue facing surface of said stapling head; a moveable shaft connecting the circular anvil and stapling head; and at least one cooled zone,
wherein the cooled zone is located inside the circular anvil in proximity to the anvil tissue facing surface,
wherein the cooled zone comprises a reservoir filled with a coolant.

2. The circular stapling instrument of claim 1, wherein said coolant is water, normal saline, any aqueous solution, alcohol, glycerol, ethylene glycol or mixtures thereof.

3. The circular stapling instrument of claim 2, wherein said coolant is a combination of a frozen coolant and a melted coolant.

4. The circular stapling instrument of claim 2, wherein said coolant is comprising a glycerol-water mixture having melting point above 0° C. but below 8° C.

5. The hypothermic surgical stapler of claim 1,
wherein the cooled zone has a temperature from −10° C. to +10° C. prior to stapling.

6. The hypothermic surgical stapler of claim 1, further comprising a probe configured to indicate temperature of said cooled zone.

7. The circular stapling instrument of claim 1, wherein said coolant is comprising an instant coolant providing cooling using an endothermic reaction.

8. The circular stapling instrument of claim 1, wherein the cooled zone comprises a Peltier element.

9. The circular stapling instrument of claim 1, wherein the cooled zone comprises a heat pipe configured to transfer thermal energy between the circular anvil and a stapler handle.

10. The circular stapling instrument of claim 1, wherein a thermally conductive zone extends from being in contact with the reservoir towards the anvil tissue facing surface and/or towards the stapling head tissue facing surface.

11. The circular stapling instrument of claim 1, wherein the reservoir has at least one window.

* * * * *